United States Patent
Siddiqui (12)

(10) Patent No.: US 6,306,140 B1
(45) Date of Patent: Oct. 23, 2001

(54) BONE SCREW

(75) Inventor: Imran Tauhid Siddiqui, Fair Oaks, CA (US)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/760,737

(22) Filed: Jan. 17, 2000

(51) Int. Cl.[7] .................................................. A61B 17/58
(52) U.S. Cl. ................................................. 606/73; 606/72
(58) Field of Search ................................. 606/73, 71, 72, 606/70, 69, 60, 65, 54, 57, 59, 232; 411/187, 389, 397, 395, 413

(56) References Cited

U.S. PATENT DOCUMENTS

| 2,382,019 | 8/1945 | Stern | 85/47 |
| 4,175,555 | * 11/1979 | Herbert | 606/73 |
| 4,463,753 | * 8/1984 | Gustillo | 606/73 |
| 4,858,601 | * 8/1989 | Glisson | 606/73 |
| 5,019,079 | * 5/1991 | Ross | 606/72 |
| 6,001,101 | * 12/1999 | Augagneur et al. | 606/73 |

FOREIGN PATENT DOCUMENTS

| 603 330 | 9/1934 | (DE) . |
| 0 669 110 A2 | 12/1995 | (EP) . |

* cited by examiner

*Primary Examiner*—Pedro Philogene
(74) *Attorney, Agent, or Firm*—Pennie & Edmonds LLP (57) ABSTRACT

The present invention relates to a implant for providing compression between different regions of material. A first embodiment of the invention relates to a implant configured to substantially prevent separation of compressed regions of material upon removing the implant. In particular, the invention relates to a compression bone screw suitable for stabilizing a fractured bone.

15 Claims, 5 Drawing Sheets

BONE SCREW

FIELD OF THE INVENTION

The present invention relates to implants for providing compression between different regions of a material. In particular, the invention relates to a compression bone screw suitable for stabilizing a fractured bone.

BACKGROUND OF THE INVENTION

Treatment of many bone disorders involves stabilizing the bone, such as by providing compression between different regions of bone thereby bringing the regions together to facilitate healing. Typically, bone screws, such as the screw device described in U.S. Pat. No. 6,001,101 to Augagneur and published application No. EP0,856,293 to Diebold et al., have utilized threaded portions having different pitches or leads to establish compression. For example, the compression effect of the Augagneur screw device arises because the travel of the distal portion is higher than the proximal portion, such that the proximal part is driven by the integral distal portion providing compression. Removal of known compression screws, however, tends to generate forces or bias generally opposing the compression achieved during insertion, which can destabilize regions of bone. Another disadvantage of known compression screws is that the threads provide insufficient surface area or purchase at large lead lengths to prevent pullout or damage to the bone.

There is a need, therefore, for an improved bone screw.

SUMMARY OF THE INVENTION

The present invention relates to an implant for insertion in a material. The implant preferably includes a longitudinal axis, a proximal portion, and a distal portion. The proximal and distal portions preferably have proximal and distal threads, respectively. The proximal and distal threads are preferably configured to threadably engage first and second spaced regions of the material, respectively, when the shaft is rotated in one direction about its longitudinal axis to bias the first and second regions of material with respect to one another to provide compression therebetween. When the shaft is rotated in an opposite direction about its longitudinal axis, the proximal thread is preferably configured to substantially inhibit biasing the first region to substantially prevent tension between the first and second regions.

At least a portion of the proximal thread is preferably tapered. For example, the tapered portion of the proximal thread preferably defines an angle of at least about twenty degrees with respect to the longitudinal axis of the shaft. In a preferred embodiment, the tapered portion of the proximal thread disengages the proximal thread from the first region of material in less than about one-half rotation of the longitudinal axis of the shaft in the opposite direction.

In a preferred embodiment, the implant is a compression bone screw and the first and second regions of material are first and second regions of bone, respectively. In the this embodiment, the implant is preferably configured to stabilize the regions of bone by providing compression therebetween and, upon removal of the implant, the implant is configured to inhibit destabilization or distraction of the regions of bone.

In another embodiment, the proximal and distal threads define proximal and distal leads, respectively, the distal lead being larger than the proximal thread. The proximal and distal portions are substantially fixed with respect to one another and preferably spaced apart by a medial portion. A proximal portion of the implant preferably includes a proximal face defining a depressed region, which includes a drive mechanism therein to receive a drive tool.

Preferably, the distal threads define a proximal face and a distal face to engage the surrounding material. The proximal face and distal faces define first and second angles, respectively, with respect to the longitudinal axis. Preferably, the second angle is smaller than the first angle.

In another embodiment, the present invention relates to an implant including a proximal portion having at least one thread configured to be accommodated within a first region of material and a distal portion having at least three thread starts and configured to be accommodated within the second region of material. Upon insertion of the implant, the proximal and distal threads preferably threadably engage the first and second regions, respectively, providing compression therebetween. Preferably, the distal threads provide sufficient purchase to substantially prevent damaging the second region of material. In a preferred embodiment, the proximal portion includes at least two thread starts, more preferably at least three thread starts. In another preferred embodiment, the distal portion preferably includes at least four thread starts.

BRIEF DESCRIPTION OF THE DRAWINGS

Preferred embodiments of the invention will now be described in connection with the attached figures, wherein.

DETAILED DESCRIPTION OF THE PREFERRED EMBODIMENTS

Referring to FIGS. 1–7, implant 1 is preferably configured to be accommodated within a material having at least first and second regions to stabilize the regions, such as by positioning and/or fixing them with respect to one another. Preferably, the implant is configured to provide compression between the regions, such as by biasing them relatively toward one another. The biasing preferably comprises providing compressive forces tending to urge the regions toward one another along a longitudinal axis 3 of implant 1. If the regions are at least somewhat fixed with respect to one another, such as regions of bone only partially separated by an incomplete fracture, the absolute motion or translation of the regions may be negligible but compressive forces tending to stabilize the regions will still be established therebetween upon installing the implant 1. In some cases, the first and second regions of material may be spaced apart by at least a third region of material, which is preferably not threadably engaged by the implant 1. In these cases, the first and second regions preferably compress the third region therebetween upon insertion of implant 1.

Figure 1:
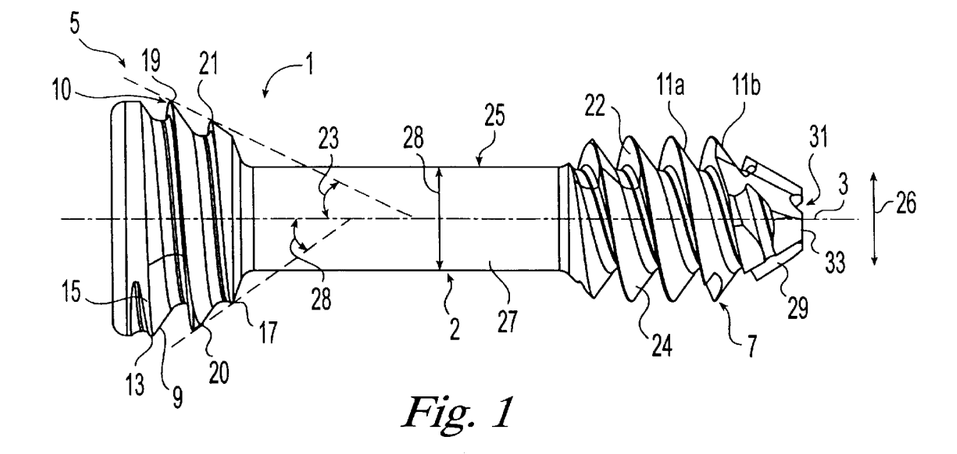
FIG. 1 is a side view of a first embodiment of an implant according to the present invention.
Figure 2:
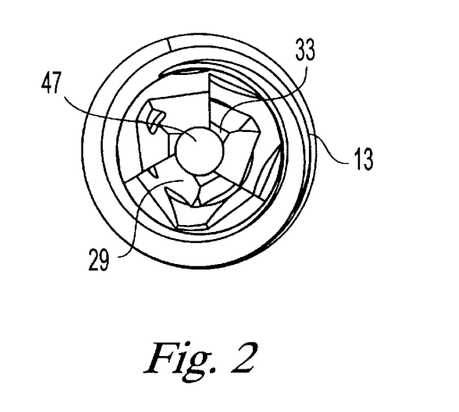
FIG. 2 is a distal end view of the implant shown in FIG. 1.
Figure 3:
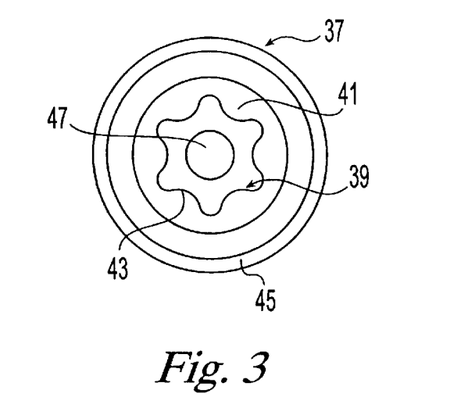
FIG. 3 is a proximal end view of the implant shown in FIG. 1.
Figure 4:
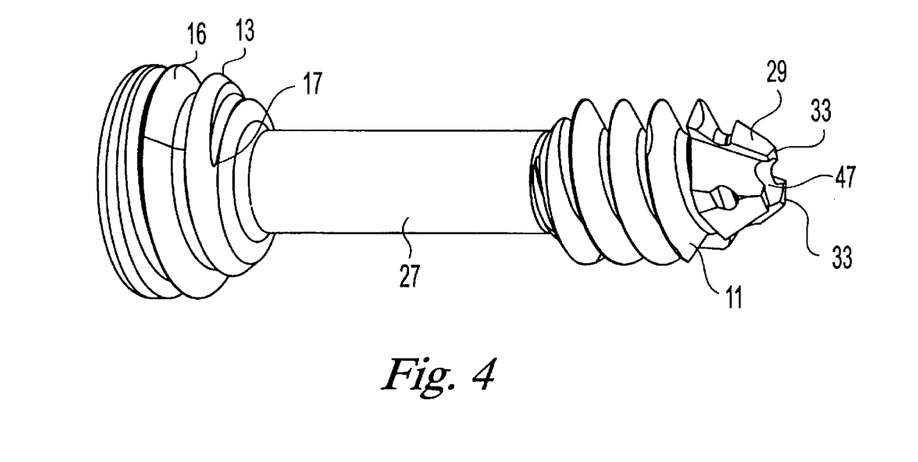
FIG. 4 is a distal perspective view of the implant shown in FIG. 1.
Figure 5:
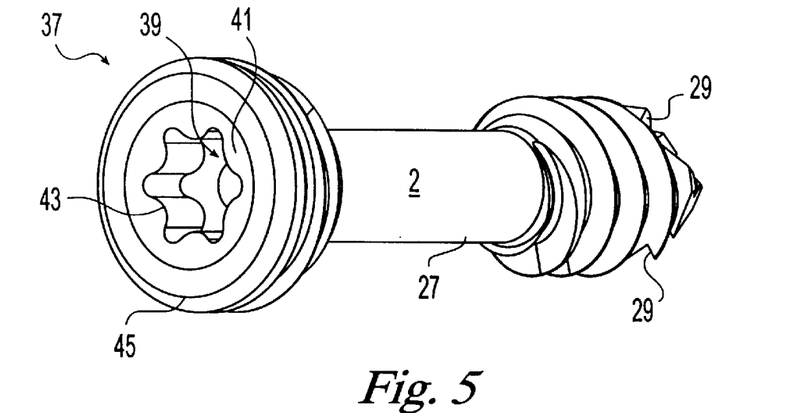
FIG. 5 is a proximal perspective view of the implant shown in FIG. 1.

The invention advantageously allows insertion and removal of implant 1 within friable and/or frangible materials without causing material damage. Preferred materials for use with the present invention include bone, masonry, stone, cement, plaster, and the like, although the implant is suitable for use within any material able to accommodate the implant.

In a preferred embodiment, the implant of the invention is a compression bone screw configured to provide compression between regions or fragments of bone that are at least partially destabilized, as by a fracture or break, such that opposed portions of the regions of bone are sufficiently adjoined to promote healing and/or stabilization of the bone. More preferably, the implant of the invention is sized and configured for insertion in bones associated with the hands or wrist, such as a scaphoid bone, or bones associated with the feet or ankles. It should be understood, however, that the invention is also adaptable for stabilizing other bones, such as long bones including the femur, tibia, or humerus. Accordingly, the implant of the invention may be formed of any bio-compatible material, such as titanium, chrome alloys, and stainless steel. Alternatively, any biodegradable and/or bioabsorbable material such as calcium phosphate or hydroxyapatite may also be used.

In the preferred embodiment, implant 1 includes a shaft 2 having proximal and distal portions 5 and 7, which include a proximal thread 9 and distal threads 11a and 11b, respectively. Preferably, proximal portion 5 includes at least a single thread start and distal portion 7 includes at least two thread starts. The number of thread starts refers to the number of preferably helical thread forms formed on the shaft. Hereinafter, the distal threads 11a and 11b are referred to by the common reference numeral 11. The pitch of distal threads 11 is preferably identical to the pitch of single proximal thread 9. Proximal and distal portions 5, 7 are preferably fixed with respect to one another and spaced apart by a distance sufficient to allow proximal and distal threads 9, 11 to be accommodated within and to become threadably engaged with the first and second regions of material, respectively. It should be understood, however, that the preferred distance separating proximal and distal portions 5, 7 depends on the dimensions and spacing of the regions of material receiving the implant.

Shaft 2 of implant 1 preferably includes a medial portion 25 interposed between and spacing apart proximal and distal portions 5, 7 and configured to bridge between the first and second regions of material upon insertion of implant 1. Preferably, medial portion 25 is configured and sized to substantially prevent proximal and distal portions 5, 7 from each engaging the same region of material to allow the different regions of material to be biased with respect to one another. Additionally, medial portion 25 is preferably configured to translate and/or rotate substantially freely with respect to surrounding regions of material upon insertion or removal of implant 1 to substantially prevent medial portion 25 from exerting a bias upon the surrounding material.

Referring to FIG. 1, medial portion 25 includes a smooth region, such as a cylinder 27, which is devoid of threads. Cylinder 27 can have a smaller outer diameter than the diameter of either of proximal threads 9 or distal threads 11. Alternatively, medial portion 25 may be tapered, bowed inwardly, or define any other shape configured to facilitate translation and/or rotation of medical portion 25 with respect to a surrounding material. Medial portion 25 may also define a region of threads or thread-like forms having a height or surface area insufficient to gain substantial purchase or engagement with the surrounding material.

Shaft 2 can includes a cannulation 47 extending along longitudinal axis 3 from a distal tip 31 to a proximal face 37 of implant 1. Distal tip 31 of implant 1 includes cutting elements 33 configured to cut material as implant 1 is inserted. Alternatively, distal tip 31 may be configured with a smooth tip, such as a hemispherical tip.

Figure 8:
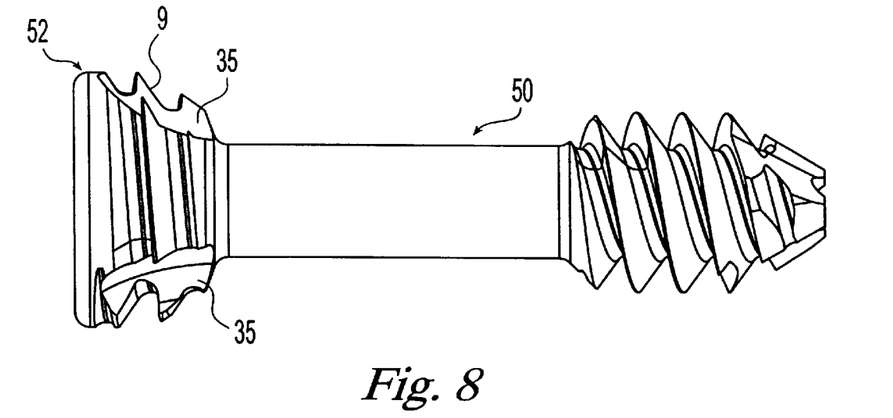
FIG. 8 is a side view of a second embodiment of an implant according to the invention.
Figure 9:
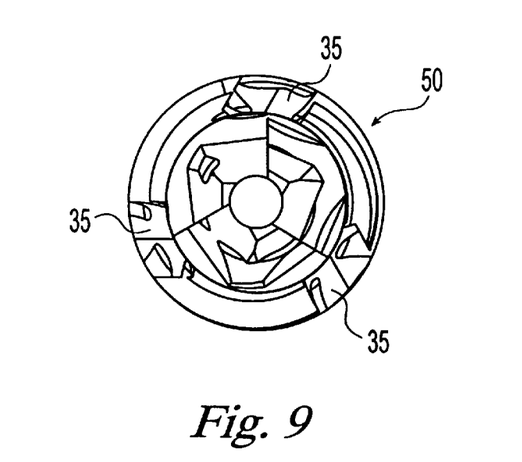
FIG. 9 is a distal end view of the implant shown in FIG. 8.

Distal portion 7 preferably includes self-cutting channels or flutes 29 disposed proximal to distal tip 31 to prepare and tap the material for distal threads 11 during insertion. Thus, in the preferred embodiment, implant 1 is both self-drilling and self-tapping such that a pilot hole having a depth equal to or greater than the length of implant 1 is not required to insert the implant 1, as discussed below. FIGS. 8 and 9 show an embodiment of an implant 50 having a proximal portion 52 provided with proximal cutting flutes 35 to prepare and tap the bone for proximal thread 9 during insertion. With the exception of proximal flutes 35, implant 50 is substantially similar to implant 1. As understood by one of ordinary skill in the art, the aggressiveness of proximal and distal cutting flutes 35, 29, as determined by the depth, angle, and number of flutes, may be adjusted to suit the characteristics of the material accommodating the implant.

Returning to the embodiment of FIGS. 1–7, proximal face 37 of implant 1 defines a centrally located drive mechanism, such as a slot or socket 39 to receive a drive tool for applying torque to implant 1 during insertion and removal. Socket 39 is preferably disposed within a concave, hemispherical depression 41 such that a proximal or upper edge 43 of the socket is disposed beneath or distal to a rim 45 of proximal face 37. Thus, rim 45 preferably defines the most proximal portion or end of the implant. During use, hemispherical depression 41 advantageously guides the drive tool toward socket 39 to prevent the drive tool from being displaced laterally into the surrounding material.

In preparation for insertion of implant 1 into, for example, a bone having first and second regions, a guide wire is preferably placed through the bone along a predetermined insertion axis. If needed, cannulated drill bit and/or cannulated countersink guided by the guide wire can then be used to form a relatively shallow pilot hole and a larger diameter, concentric countersink in the bone fragment. To minimize loss of material, the pilot hole is preferably only deep enough to allow cutting elements 33 and flutes 29 to engage the bone to prepare the bone for distal threads 11 upon rotation of implant 1. The countersink preferably defines a sufficient diameter to allow proximal cutting flutes 35, if included, to engage the bone to prepare the bone for proximal thread 9 once the implant has reached a sufficient depth.

Upon continued rotation of implant 1 in a first orientation about longitudinal axis 3, such as, for example, clockwise, threads 9 and 11 threadably engage the first and second regions, respectively, such that proximal portion 5 and the first region of bone are biased in a first direction at a first rate relative to one another and distal portion 7 and the second region of bone are biased in a second direction at a second rate relative to one another. In general, the rate at which a threaded element that is threadably engaged with a region of material biases that region of material is defined herein as the distance relative to the material and parallel to the longitudinal axis of the element that the region of material is urged to translate upon one rotation of the threaded element. The rate that implant 1 biases a first region of material engaged with proximal threads 9 with respect to a second region of material engaged with distal threads 11 is equivalent to the difference in the number of proximal and distal thread starts multiplied by the pitch of the threads.

The first and second directions of bias imparted by implant 1 are preferably the same in an absolute sense. The rates of bias of proximal and distal threads 9, 11, however, are preferably different to provide a desired compression between the first and second regions of material upon rotation of implant 1. Preferably, distal portion 7 has a greater number of thread starts than proximal portion 5 to bias the second region of material at a greater rate than the rate at which proximal portion 5 biases the first region of material. Upon insertion, therefore, the differential bias preferably provides an amount of compression sufficient to bring the first and second regions of material into stable contact with one another to promote stabilization and healing.

Proximal and distal threads 9, 11 are configured to substantially prevent threads 9, 11 from stripping, pulling out, or otherwise damaging a threadably engaged region of material upon installing or removing implant 1. By "substantially prevent" it is meant that implant 1 may be inserted, such as by applying torque, to provide a desired degree of compression between the first and second regions without loss of purchase or engagement between implant 1 and the material. Thus, because damage to the threadably engaged material is substantially prevented, the compression established during insertion of implant 1 is substantially maintained after insertion is completed.

Figure 7:
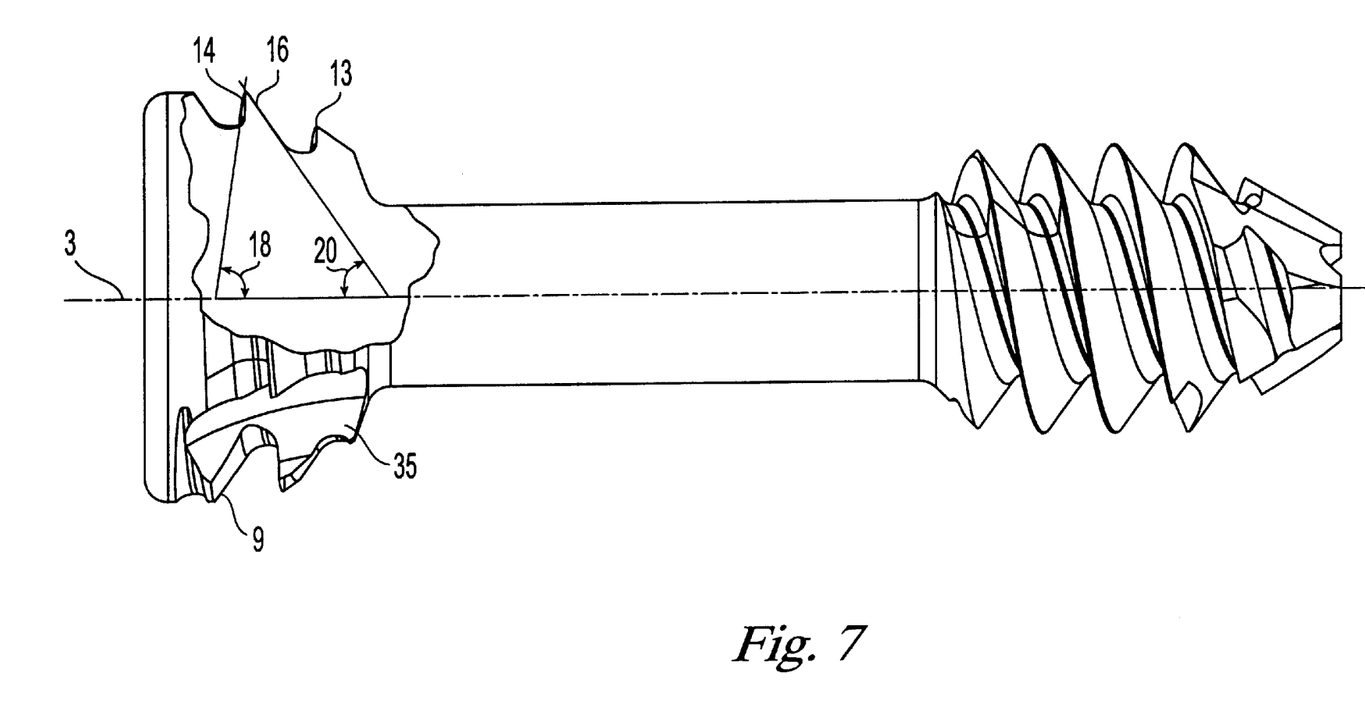
FIG. 7 shows a partial side view of the implant shown in FIG. 1 with a section of the proximal portion cutaway.

Threads 9, 11 preferably define at least about one complete revolution and, more preferably, at least about one and one half complete revolutions about implant 1 to increase engagement between the threads 9,11 and the surrounding material. As best seen in FIG. 7, proximal thread 9 includes a proximal face 14 and a distal face 16, which act to transfer forces between threads 9 and a surrounding material. Proximal and distal faces 14, 16 define angles 18 and 20, respectively, with respect to longitudinal axis 3 of implant 1. Angle 18 is preferably larger than angle 20 to provide more efficient transfer of forces between threads 9 of implant 1 and a surrounding material during insertion to inhibit damage to the surrounding material during compression.

FIG. 1 shows that a proximal face 22 and a distal face 24 of distal threads 11 are configured similarly to proximal and distal faces 14, 16 of proximal threads 9. To further enhance the engagement of distal threads 11 with the surrounding material, the root diameter 26 of distal threads 11 may be smaller than the diameter 28 of medial portion 25. Thus, because the outer diameter of distal threads 11 is larger than medial diameter 28, proximal and distal faces 22, 24 present a larger surface area to the surrounding material.

Upon removal, such as by applying torque to implant 1 in an opposite orientation from the torque applied during insertion, implant 1 is configured to substantially eliminate bias tending to urge the first and second regions of material apart from one another. Such bias undesirably places the implant under compression and the first and second regions under tension, which increases the tendency of the first and second regions to separate or become destabilized with respect to one another. Preferably, proximal thread 9 disengages the first region of material in less than about one-half rotation, more preferably in less than one-quarter rotation of implant 1. By disengages, it is meant that proximal thread 9 substantially ceases to exert a bias upon the first region of material as rotation and removal progress. Thus, in the preferred embodiment, implant 1 substantially prevents forces tending to distract or destabilize a healed or stabilized bone such that compressed fragments of bone remain stabilized or adjoined upon removal of implant 1.

Referring to FIG. 1, proximal thread 9 includes an outwardly tapering crest 13 having proximal and distal ends 15, 17. Proceeding along crest 13 from distal end 17 toward proximal end 15, at least a portion of crest 13 tapers generally outward such that proximal end 15 defines a larger diameter than distal end 17. Preferably, all of the proximal threads are tapered. The outward taper of proximal thread 9 is preferably sufficient to disengage the surrounding material upon removal, as described above. Preferably, crest 13 includes at least two adjacent points 19, 21 that define an angle 23 of at least about 15°, preferably at least about 20°, and more preferably at least about 25° with respect to longitudinal axis 3 of shaft 2. Adjacent points 19, 21 are preferably separated from one another by one complete rotation of thread 9 about shaft 2. Point 21 is preferably separated from distal end 17 by at least about one complete rotation of thread 9 about shaft 2. Distal end 17 and an adjacent point 20 on thread crest 13 preferably define an angle of at least about 30° with respect to longitudinal axis of shaft 2.

Proximal threads 9 preferably extend sufficiently far toward proximal face 37 that implant 1 may be inserted so as to prevent any protrusion of implant 1 above the surface of a material. Thus, for example, the present invention may be inserted through a region, such as a joint, adjoining different bones without perturbing the relative motion of the bones.

Figure 6A:
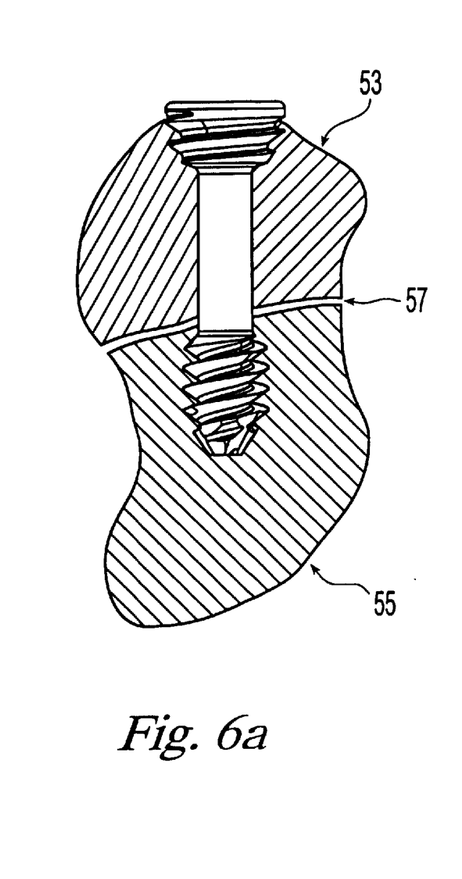
FIG. 6a shows a cross-sectional side-view of the implant implanted in a scaphoid in a partially inserted state.
Figure 6B:
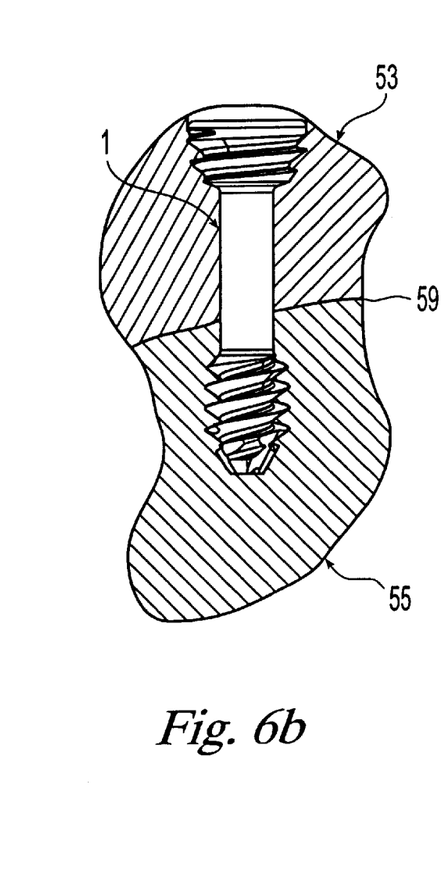
FIG. 6b shows a cross-sectional side-view of the implant implanted in a scaphoid in a fully inserted state.
Figure 6C:
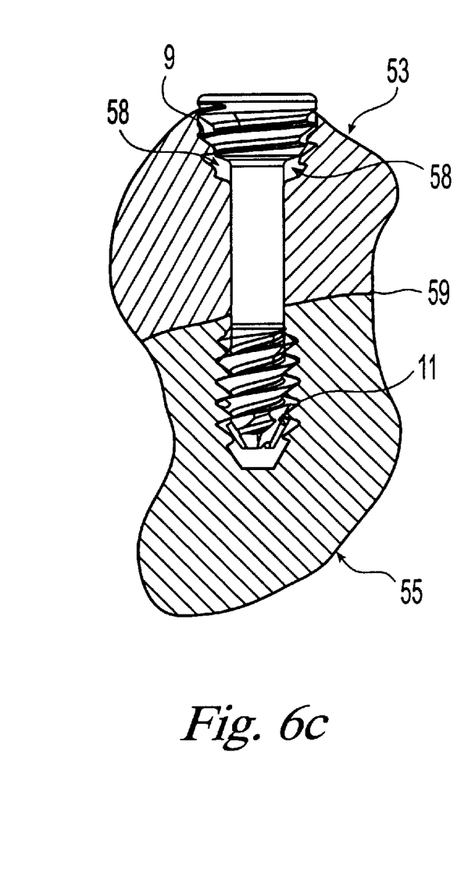
FIG. 6c shows a cross-sectional side-view of the implant implanted in a scaphoid in a partially removed state.

Referring to FIGS. 6a–6c, the implant 1 is shown in an exemplary use for insertion into a scaphoid bone 51, having first and second regions 53, 55 associated with a region of instability, such as a fracture 57. Prior to complete insertion of implant 1, fracture 57 typically separates first and second regions 53, 55, as shown in FIG. 6a. At this stage, proximal and distal threads are threadably engaged with the first and second regions 53, 55, respectively, of scaphoid 51. Continued rotation of implant 1 biases first and second regions 53, 55 toward one another. Implant 1 is inserted into scaphoid 51 to a depth sufficient to stabilize the region of instability, such as by providing sufficient compression to substantially close fracture 57, as shown in FIG. 6b. Substantial closure of fracture 57 provides an adjoined region 59 where first and second regions 53, 55 are positioned in sufficiently close opposition to promote stabilization, such as by healing or knitting, of fracture 57. FIG. 6c shows the implant in a partial state of removal with proximal threads 9 disengaged from first region 53 of scaphoid 51 leaving a gap 58 therebetween to prevent proximal threads 9 from exerting a bias upon first region 53 of material. Subsequent to complete removal, therefore, first and second regions 53, 55 will remain stably adjoined.

Figure 10:
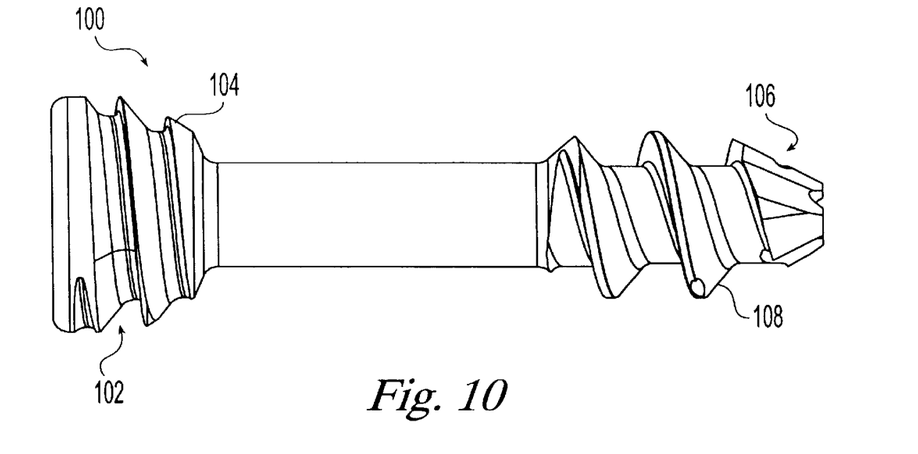
FIG. 10 shows a side view of a third embodiment of an implant according to the invention.

A second embodiment of an implant 100 shown in FIG. 10 includes a proximal portion 102 and a distal portion 106.

Proximal and distal portions 102, 106 include a single proximal thread form 104 and a single distal thread form 108. Proximal thread 104 of implant 100 preferably defines an outward taper sufficient to prevent undesirable bias upon removal, as discussed above.

Proximal and distal portions 102, 106 of implant 100 are configured to be accommodated within first and second regions of material, respectively, to provide compression or tension therebetween, as described above. Because proximal and distal portions 102, 106 are each provided with only a single thread start, however, the pitch of proximal thread 104 is preferably different from the pitch of distal thread 108 such that proximal portion 102 is urged to advance at a different rate with respect to a surrounding material than is distal portion 106 upon rotation of implant 100. Preferably, the pitch of distal thread 108 is greater than the pitch of proximal thread 104 to provide compression upon insertion of implant 100. With the exception that implant 100 includes only a single distal thread 108 start, implant 100 preferably includes features substantially similar to those described above for implant 1.

Figure 11:
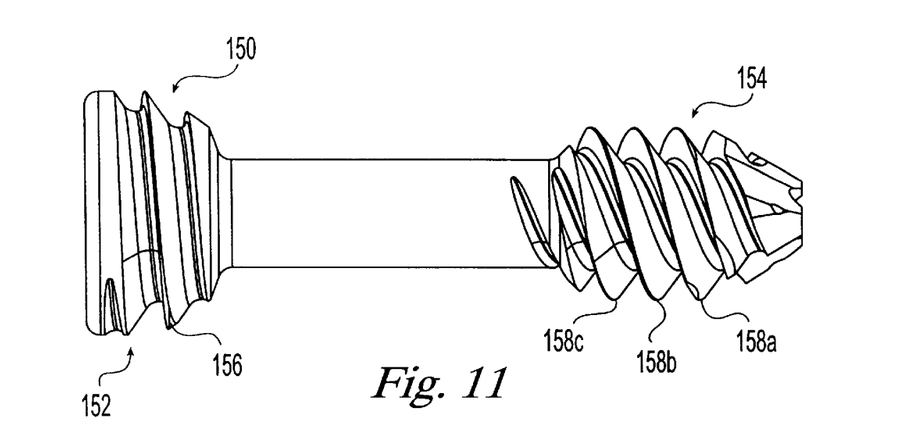
FIG. 11 is a side view of a fourth embodiment of an implant according to the invention.

A third embodiment of an implant 150 shown in FIG. 11 includes a proximal portion 152 and a distal portion 154. Distal portion 154 of implant 150 preferably includes a sufficient number of distal thread starts to increase engagement and purchase of the distal threads with a surrounding material to prevent damage thereto and maintain compression subsequent to installation if implant 150. Preferably, distal portion 154 includes at least three distal thread forms 158a–158c having at least three thread starts and more preferably at least four thread starts. Proximal thread 156 of proximal portion 152 preferably includes at least one proximal thread start. Implant 150 may also be provided with features similar to those described above, such as, for example, a proximal taper, medial portion, and cutting flutes.

In addition to providing greater purchase with the surrounding material, including additional threads on the proximal and distal portions allows greater precision and choice in selecting a degree of compression for a given application. For example, Table 1 shows the absolute compression in millimeters that can be obtained for an implant having proximal and distal thread pitch of 0.25 mm, and Table 2 shows the absolute compression that can be obtained for an implant having a proximal and distal thread pitch of 0.67 mm. Here, the absolute compression is defined as the distance translated by the distal portion minus the distance translated by the proximal portion upon one rotation of the implant. The absolute compression, therefore, corresponds to the relative change in separation distance of a freely translating region of material engaged with the proximal portion with respect to a second freely translating region of material engaged with the distal portion upon one complete rotation of the implant.

Figure 12:
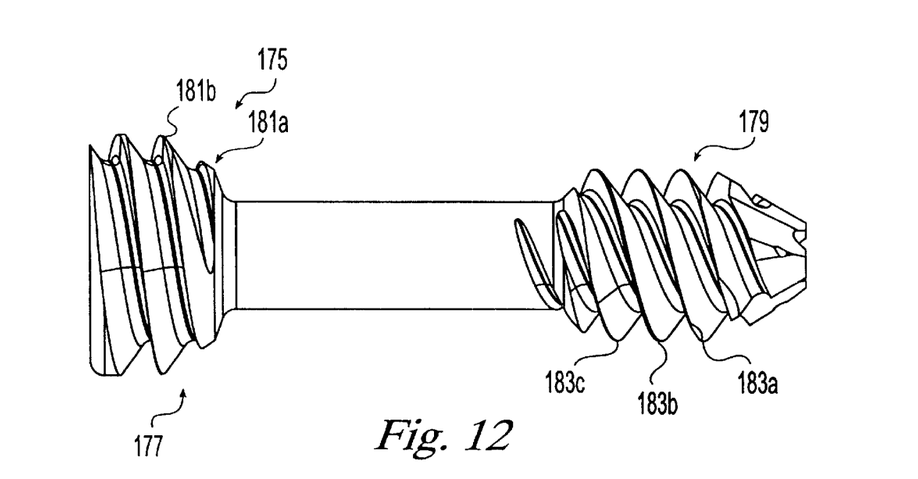
FIG. 12 is a side view of a fifth embodiment of an implant according to the invention.

Positive values in Tables 1 and 2 indicate combinations of proximal and distal thread starts wherein compression is achieved upon insertion of the implant, while negative values indicate regions wherein tension results upon insertion of the implant. By varying the number of distal and proximal thread starts, the compression can be varied. For example, referring to Table 2, an implant having three distal thread starts and two proximal thread starts having a pitch of 0.67 mm provides an absolute compression of 0.67 mm for each rotation of the implant. FIG. 12, shows an embodiment of an implant 175 having a proximal portion 177 including first and second proximal thread starts 181a–181b and a distal portion 179 including three distal thread starts 183a–183c. The embodiment of FIG. 12 would provide significantly greater purchase than an implant having fewer threads while achieving and maintaining a sufficient amount of compression. Thus, according to the present invention, an implant may include from 1–7 distal threads and from 1–6 proximal threads configured to provide compression.

It will be appreciated that those skilled in the art may devise numerous modifications and embodiments. It is intended that the following claims cover all such modifications and embodiments that fall within the true spirit and scope of the present invention. For example, the implant may be configured to provide tension between the regions of material, such as by biasing them apart upon insertion of the implant. In this case, the implant could be configured to prevent compression of the spaced apart regions upon removal of the implant.

TABLE 1

Compression Obtained for a Screw With a Pitch of 0.25 Millimeters

| Number of Proximal Thread Starts | Number of Distal Thread Starts | | | | | | |
|---|---|---|---|---|---|---|---|
| | 1 | 2 | 3 | 4 | 5 | 6 | 7 |
| 1 | 0 | 0.25 | 0.5 | 0.75 | 1 | 1.25 | 1.5 |
| 2 | −0.25 | 0 | 0.25 | 0.5 | 0.75 | 1 | 1.25 |
| 3 | −0.5 | −0.25 | 0 | 0.25 | 0.5 | 0.75 | 1 |
| 4 | −0.75 | −0.5 | −0.25 | 0 | 0.25 | 0.5 | 0.75 |
| 5 | −1 | −0.75 | −0.5 | −0.25 | 0 | 0.25 | 0.5 |
| 6 | −1.25 | −1 | −0.75 | −0.5 | −0.25 | 0 | 0.25 |
| 7 | −1.5 | −1.25 | −1 | −0.75 | −0.5 | −0.25 | 0 |

TABLE 2

Compression Obtained for a Screw With a Pitch of 0.67 Millimeters

| Number of Proximal Thread Starts | Number of Distal Thread Starts | | | | | | |
|---|---|---|---|---|---|---|---|
| | 1 | 2 | 3 | 4 | 5 | 6 | 7 |
| 1 | 0.00 | 0.67 | 1.33 | 2.00 | 2.67 | 3.33 | 4.00 |
| 2 | −0.67 | 0.00 | 0.67 | 1.33 | 2.00 | 2.67 | 3.33 |
| 3 | −1.33 | −0.67 | 0.00 | 0.67 | 1.33 | 2.00 | 2.67 |
| 4 | −2.00 | −1.33 | −0.67 | 0.00 | 0.67 | 1.33 | 2.00 |
| 5 | −2.67 | −2.00 | −1.33 | −0.67 | 0.00 | 0.67 | 1.33 |
| 6 | −3.33 | −2.67 | −2.00 | −1.33 | −0.67 | 0.00 | 0.67 |
| 7 | −4.00 | −3.33 | −2.67 | −2.00 | −1.33 | −0.67 | 0.00 |

What is claimed is:

1. An implant for insertion in a material, the implant comprising:
   a shaft including a longitudinal axis, a proximal portion, and a distal portion, the proximal and distal portions having proximal and distal threads, respectively;
   with the proximal and distal threads being configured to threadably engage first and second spaced regions of the material, respectively, when the shaft is rotated in one direction about its longitudinal axis to bias the first and second regions of material with respect to one another to provide compression therebetween, and the proximal thread is configured to substantially inhibit biasing the first region when the shaft is rotated in an opposite direction about its longitudinal axis to substantially prevent tension between the first and second regions.

2. The implant of claim 1, wherein a portion of the proximal thread is tapered.

3. The implant of claim 2, wherein the tapered portion of the proximal thread defines an angle of at least about twenty degrees with respect to the longitudinal axis of the shaft.

4. The implant of claim 2, wherein the tapered portion of the proximal thread disengages the proximal thread from the first region of material in less than about one-half rotation of the longitudinal axis of the shaft.

5. The implant of claim 1, wherein the shaft further comprises a medial portion disposed between and spacing apart the proximal and distal portions.

6. The implant of claim 1, wherein the implant is a compression bone screw and the first and second regions of material are first and second regions of bone, respectively, and further wherein, upon insertion, the implant is configured to stabilize the regions of bone by providing compression therebetween and, upon removal of the implant, the implant is configured to inhibit destabilization of the regions of bone.

7. The implant of claim 1, wherein the distal portion comprises at least two distal thread starts, the distal threads defining a larger lead than the proximal threads.

8. The implant of claim 1, wherein the proximal and distal portions are substantially fixed with respect to one another.

9. The implant of claim 1, wherein the proximal portion includes a proximal face, the proximal face including a depressed region defining a drive mechanism therein.

10. The implant of claim 1, wherein the distal threads define a proximal face and a distal face, the proximal face defining a first angle with respect to the longitudinal axis and the distal face defining a second, smaller angle with respect to the longitudinal axis.

11. An implant for insertion in a material having first and second regions, the implant comprising:
 a proximal portion having at least one thread start, the proximal thread configured to be accommodated within the first region of material;
 a distal portion having at least three thread starts, the distal threads configured to be accommodated within the second region of material; and
 wherein, upon insertion of the implant by rotation, the proximal and distal threads threadably engage the first and second regions, respectively, to provide compression therebetween, the distal threads providing sufficient purchase to substantially prevent damaging the second region of material.

12. The implant of claim 11, wherein the proximal portion includes at least two thread starts.

13. The implant of claim 12, wherein the proximal portion includes at least three thread starts.

14. The implant of claim 13, wherein the distal portion includes at least four thread starts.

15. The implant of claim 11, wherein the implant defines a longitudinal axis and further wherein the distal threads define a proximal face and a distal face, the proximal face defining a first angle with respect to the longitudinal axis and the distal face defining a second, smaller angle with respect to the longitudinal axis.

\* \* \* \* \*

UNITED STATES PATENT AND TRADEMARK OFFICE
CERTIFICATE OF CORRECTION

PATENT NO. : 6,306,140 B1
DATED : October 23, 2001
INVENTOR(S) : Imran Siddiqui

It is certified that error appears in the above-identified patent and that said Letters Patent is hereby corrected as shown below:

<u>Title page,</u>
Replace Item [22] with:
-- [22]  Filed:  Jan. 17, 2001 --

Signed and Sealed this

Thirtieth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,306,140 B1
DATED : October 23, 2001
INVENTOR(S) : Imran Siddiqui

It is certified that error appears in the above-identified patent and that said Letters Patent is hereby corrected as shown below:

Title page,
Item [56], References Cited, replace with:

U.S. PATENT DOCUMENTS

| | | | |
|---|---|---|---|
| 1,135,516 | | 4/1915 | Frauenheim | |
| 1,926,925 | | 9/1933 | Wescott | 287/125 |
| 2,060,593 | | 11/1936 | Schaurte et al. | 10/27 |
| 2,123,764 | | 7/1938 | Berry | 85/32 |
| 2,267,925 | | 12/1941 | Johnston | 128/92 |
| 2,382,019 | * | 8/1945 | Miller | 85/41 |
| 2,570,465 | | 10/1951 | Lundholm | 128/92 |
| 3,051,169 | | 8/1962 | Grath | 128/92 |
| 3,256,661 | | 6/1966 | Fischer | 52/373 |
| 3,499,222 | | 3/1970 | Linkow et al. | 13/22 |
| 3,541,918 | | 11/1970 | Johnson | 85/46 |
| 3,682,507 | | 8/1972 | Waud | 287/189 |
| 3,867,932 | | 2/1975 | Huene | 128/92 |
| 4,016,874 | | 4/1977 | Maffei et al. | 128/92 |
| 4,175,555 | * | 11/1979 | Herbert | 128/92 |
| 4,259,072 | | 3/1981 | Hirabayashi et al. | 433/173 |
| 4,463,753 | * | 8/1984 | Gustilo | 128/92 |
| 4,537,185 | | 8/1985 | Stednitz | 128/92 |
| 4,576,534 | | 3/1986 | Barth et al. | 411/412 |
| 4,621,963 | | 11/1986 | Reinwall | 411/369 |
| 4,640,271 | | 2/1987 | Lower | 128/92 |
| 4,754,749 | | 7/1988 | Tsou | 128/92 |
| 4,790,850 | | 12/1988 | Dunn et al. | 623/13 |
| 4,858,601 | * | 8/1989 | Glisson | 606/73 |
| 4,861,206 | | 8/1989 | Riedel | 411/36 |
| 4,870,957 | | 10/1989 | Goble et al. | 128/92 |
| 4,877,364 | | 10/1989 | Sorrentino | 411/337 |
| 4,878,793 | | 11/1989 | Hewison | 411/387 |
| 4,927,421 | | 5/1990 | Goble et al. | 606/73 |
| 4,950,270 | | 8/1990 | Bowman et al. | 606/72 |
| Re 33,348 | | 9/1990 | Lower | 606/65 |
| 4,959,938 | | 10/1990 | De Caro | 52/410 |
| 4,963,144 | | 10/1990 | Huene | 606/73 |
| 4,966,024 | | 10/1990 | Hewison | 72/88 |

UNITED STATES PATENT AND TRADEMARK OFFICE
CERTIFICATE OF CORRECTION

PATENT NO. : 6,306,140 B1
DATED : October 23, 2001
INVENTOR(S) : Imran Siddiqui

It is certified that error appears in the above-identified patent and that said Letters Patent is hereby corrected as shown below:

U.S. PATENT DOCUMENTS, cont'd,

| | | | |
|---|---|---|---|
| 5,019,079 | * | 5/1991 | Ross ................... 606/72 |
| 5,100,405 | | 3/1992 | McLaren ................ 606/72 |
| 5,116,337 | | 5/1992 | Johnson ................ 606/73 |
| 5,120,171 | | 6/1992 | Lasner ................. 411/308 |
| 5,139,499 | | 8/1992 | Small et al. ........... 606/73 |
| 5,139,520 | | 8/1992 | Rosenberg .............. 623/13 |
| 5,151,104 | | 9/1992 | Kenna .................. 606/73 |
| 5,152,764 | | 10/1992 | Goble ................. 606/96 |
| 5,156,616 | | 10/1992 | Meadows et al. ........ 606/232 |
| 5,169,400 | | 12/1992 | Mühling et al. ........ 606/73 |
| 5,180,382 | | 1/1993 | Frigg et al. .......... 606/65 |
| 5,188,496 | | 2/1993 | Giannuzzi ............. 411/386 |
| 5,190,544 | | 3/1993 | Chapman et al. ........ 606/69 |
| 5,201,735 | | 4/1993 | Chapman et al. ........ 606/67 |
| 5,217,462 | | 6/1993 | Asnis et al. .......... 606/73 |
| 5,226,766 | | 7/1993 | Lasner ................ 411/308 |
| 5,259,398 | | 11/1993 | Vrespa ............... 128/898 |
| 5,300,076 | | 4/1994 | Leriche .............. 606/73 |
| 5,312,412 | | 5/1994 | Whipple .............. 606/96 |
| 5,324,199 | | 6/1994 | Branemark ............ 433/174 |
| 5,358,367 | | 10/1994 | Yang ................ 411/397 |
| 5,360,448 | | 11/1994 | Thramann ............ 623/16 |
| 5,362,236 | | 11/1994 | Branemark ........... 433/173 |
| 5,364,400 | | 11/1994 | Rego, Jr. et al. .... 606/72 |
| 5,417,533 | | 5/1995 | Lasner .............. 411/426 |
| 5,433,570 | | 7/1995 | Köppel .............. 411/392 |
| 5,443,509 | | 8/1995 | Boucher et al. ...... 623/16 |
| 5,456,685 | | 10/1995 | Huebner ............ 606/73 |
| 5,492,442 | | 2/1996 | Lasner ............. 411/426 |
| 5,496,326 | | 3/1996 | Johnson ............ 606/88 |
| 5,536,127 | | 7/1996 | Pennig ............. 411/413 |
| 5,544,993 | | 8/1996 | Härle .............. 411/414 |
| 5,562,672 | | 10/1996 | Huebner et al. .... 606/73 |
| 5,607,428 | | 3/1997 | Lin ............... 606/69 |
| 5,658,288 | | 8/1997 | Kim ............... 606/64 |
| 5,735,898 | | 4/1998 | Brånemark ........ 623/16 |
| 5,743,908 | | 4/1998 | Kim .............. 606/64 |
| 5,842,865 | | 12/1998 | Bassett et al. ... 433/174 |
| 5,865,584 | | 2/1999 | Onofrio .......... 411/411 |
| 5,868,749 | | 2/1999 | Reed ............. 606/76 |
| 5,871,486 | | 2/1999 | Huebner et al. ... 606/73 |
| 5,882,162 | | 3/1999 | Kaneko ........... 411/411 |
| 5,899,906 | | 5/1999 | Schenk ........... 606/73 |
| 5,925,048 | | 7/1999 | Ahmad et al. ..... 606/73 |
| 5,947,965 | | 9/1999 | Bryan ............ 606/61 |
| 5,968,047 | | 10/1999 | Reed ............ 606/76 |
| 6,001,101 | * | 12/1999 | Augagneur et al. . 606/73 |
| 6,030,162 | | 2/2000 | Huebner ......... 411/413 |
| 6,059,785 | | 5/2000 | Schavan et al. .. 606/73 |

UNITED STATES PATENT AND TRADEMARK OFFICE
CERTIFICATE OF CORRECTION

PATENT NO.    : 6,306,140 B1
DATED         : October 23, 2001
INVENTOR(S)   : Imran Siddiqui It is certified that error appears in the above-identified patent and that said Letters Patent is hereby corrected as shown below:

FOREIGN PATENT DOCUMENTS

| | | |
|---|---|---|
| 603 330 | 9/1934 | (DE) |
| 484,654 | 5/1938 | (UK) |
| 1 162 124 | 2/1984 | CN) |
| 0 276 153 | 7/1988 | (EP) |
| WO 90/02526 | 3/1990 | (WO) |
| 0 451 932 A1 | 10/1991 | (EP) |
| WO 91/09572 | 7/1991 | (WO) |
| 0 491 211 A1 | 11/1991 | (EP) |
| 0 471 419 A2 | 2/1992 | (EP) |
| WO 93/15682 | 8/1993 | (WO) |
| 0 657 142 A1 | 11/1994 | (EP) |
| 0 669 110 A2 | 2/1995 | (EP) |
| 0 574 517 B1 | 5/1995 | (EP) |
| 0 682 917 A1 | 11/1995 | (EP) |
| 0 695 537 A1 | 2/1996 | (EP) |
| 195 29 901 A1 | 2/1996 | (DE) |
| 08052156 | 2/1996 | (JP) |
| 0 726 064 A2 | 8/1996 | (EP) |
| 08229051 | 9/1996 | (JP) |
| 09000539 | 1/1997 | (JP) |
| 10052439 | 2/1998 | (JP) |
| 10243953 | 7/1998 | (JP) |
| 0 856 293 A1 | 8/1998 | (EP) |
| 10277052 | 10/1998 | (JP) |
| 0 941 705 A2 | 9/1999 | (EP) |

\* cited by examiner

Signed and Sealed this

Sixteenth Day of December, 2003

JAMES E. ROGAN
*Director of the United States Patent and Trademark Office*